(12) United States Patent
Shambroom et al.

(10) Patent No.: US 7,161,362 B2
(45) Date of Patent: Jan. 9, 2007

(54) SYSTEM AND METHOD FOR MEASURING BIOELECTRIC IMPEDANCE IN THE PRESENCE OF INTERFERENCE

(75) Inventors: John R. Shambroom, Arlington, MA (US); Charles P. Smith, Medway, MA (US)

(73) Assignee: Aspect Medical Systems, Inc., Newton, MA (US)

( * ) Notice: Subject to any disclaimer, the term of this patent is extended or adjusted under 35 U.S.C. 154(b) by 0 days.

(21) Appl. No.: 11/105,960

(22) Filed: Apr. 14, 2005

(65) Prior Publication Data

US 2005/0203437 A1   Sep. 15, 2005

Related U.S. Application Data

(62) Division of application No. 10/190,246, filed on Jul. 3, 2002, now Pat. No. 6,882,166.

(60) Provisional application No. 60/303,531, filed on Jul. 6, 2001.

(51) Int. Cl.
*G01R 27/08* (2006.01)
*A61B 5/05* (2006.01)

(52) U.S. Cl. ...................... 324/692; 600/547

(58) Field of Classification Search ............... 324/692, 324/691, 649, 600, 613, 614, 603, 606, 76.28, 324/76.39, 76.41–3, 76.11, 76.19; 600/300, 600/398, 400, 442, 506, 533, 536, 547; 606/34, 606/38, 50, 40, 42; 607/5, 8, 45, 28, 101, 607/121, 148, 154
See application file for complete search history.

(56) References Cited

U.S. PATENT DOCUMENTS

| | | | |
|---|---|---|---|
| 4,424,816 A | | 1/1984 | Callaghan et al. |
| 4,814,934 A | * | 3/1989 | Jones et al. ................... 361/88 |
| 4,926,880 A | | 5/1990 | Claude et al. |
| 5,025,784 A | | 6/1991 | Shao et al. |
| 5,201,808 A | | 4/1993 | Steinhaus et al. |
| 5,404,877 A | | 4/1995 | Nolan et al. |
| 5,437,662 A | | 8/1995 | Nardella |
| 5,469,859 A | * | 11/1995 | Tsoglin et al. .............. 600/536 |
| 5,540,684 A | | 7/1996 | Hassler, Jr. |
| 5,808,895 A | | 9/1998 | Ibrahim et al. |
| 5,817,093 A | | 10/1998 | Williamson et al. |
| 5,963,159 A | * | 10/1999 | Abughazaleh et al. ...... 341/139 |
| 6,047,208 A | * | 4/2000 | Flower ......................... 604/20 |
| 6,049,257 A | * | 4/2000 | Hauk .......................... 332/127 |
| 6,059,780 A | | 5/2000 | Gough et al. |

(Continued)

FOREIGN PATENT DOCUMENTS

| | | |
|---|---|---|
| JP | 10-014898 | 4/1998 |
| WO | WO 95/35060 | 12/1995 |
| WO | WO 00/79255 | 12/2000 |

*Primary Examiner*—Andrew H. Hirshfeld
*Assistant Examiner*—Hoai-An D. Nguyen
(74) *Attorney, Agent, or Firm*—Wilmer Cutler Pickering Hale and Dorr LLP

(57) ABSTRACT

A system for measuring bioelectric impedance in real time, in the presence of interference and noise is disclosed. A small electric current is injected into a biopotential electrode system, and then the measurement is tested for contamination by electrical interference or other noise sources.

4 Claims, 6 Drawing Sheets

U.S. PATENT DOCUMENTS

| | | |
|---|---|---|
| 6,095,987 A | 8/2000 | Shmulewitz et al. |
| 6,203,541 B1 | 3/2001 | Keppel |
| 6,366,813 B1 | 4/2002 | DiLorenzo |
| 6,409,722 B1 * | 6/2002 | Hoey et al. .................. 606/34 |
| 6,434,707 B1 * | 8/2002 | Eklof ......................... 713/500 |
| 6,473,641 B1 | 10/2002 | Kodama et al. |
| 6,532,384 B1 | 3/2003 | Fukuda |
| 6,560,480 B1 | 5/2003 | Nachaliel et al. |
| 6,577,897 B1 | 6/2003 | Shurubura et al. |
| 6,622,035 B1 | 9/2003 | Merilainen et al. |
| 6,633,777 B1 | 10/2003 | Szopinski |
| 6,682,527 B1 | 1/2004 | Strul |
| 2002/0095145 A1 | 7/2002 | Simons et al. |
| 2002/0133152 A1 | 9/2002 | Strul |

\* cited by examiner

SYSTEM AND METHOD FOR MEASURING BIOELECTRIC IMPEDANCE IN THE PRESENCE OF INTERFERENCE

CROSS REFERENCE TO RELATED APPLICATION

This application claims priority under 35 U.S.C. 119(e) to U.S. Provisional Application Ser. No. 60/303,531 filed Jul. 6, 2001.

BACKGROUND OF THE INVENTION

Biopotential patient monitors typically use surface electrodes to make measurements of bioelectric potentials such as electrocardiogram (ECG) or electroencephalogram (EEG). The fidelity of these measurements is limited by the effectiveness of the connection of the electrode to the patient. The resistance of the electrode system to the flow of electric currents, known as the electric impedance, characterizes the effectiveness of the connection. Typically, the higher the impedance, the lower the fidelity of the measurement. Several mechanisms may contribute to lower fidelity.

Signals from electrodes with high impedances are subject to thermal noise (or so called Johnson noise), voltages that increase with the square root of the impedance value. In addition, biopotential electrodes tend to have voltage noises in excess of that predicted by Johnson. Also, amplifier systems making measurements from biopotential electrodes tend to have degraded performance at higher electrode impedances. The impairments are characterized by poor common mode rejection, which tends to increase the contamination of the bioelectric signal by noise sources such as patient motion and electronic equipment that may be in use on or around the patient. These noise sources are particularly prevalent in the operating theatre and may include equipment such as electrosurgical units (ESU), cardiopulmonary bypass pumps (CPB), electric motor-driven surgical saws, lasers and other sources.

It is often desirable to measure electrode impedances continuously in real time while a patient is being monitored. To do this, a very small electric current is typically injected through the electrodes and the resulting voltage measured, thereby establishing the impedance using Ohm's law. This current may be injected using DC or AC sources. It is often not possible to separate voltage due to the electrode impedance from voltage artifacts arising from interference. Interference tends to increase the measured voltage and thus the apparent measured impedance, causing the biopotential measurement system to falsely detect higher impedances than are actually present. Often such monitoring systems have maximum impedance threshold limits that may be programmed to prevent their operation when they detect impedances in excess of these limits. This is particularly true of systems that make measurements of very small voltages, such as the EEG. Such systems require very low electrode impedances. It is therefore desirable to develop a system that is very robust in the presence of these contaminating noise sources, thereby enabling accurate measurements.

SUMMARY OF THE INVENTION

Accordingly, a system and method is provided for measuring bioelectric impedance in real time in the presence of interference and noise. A small electric current is injected into a biopotential electrode system and the impedance measurement is tested for contamination by an electrical interference and other noise sources. The impedance is measured continuously at the frequency of the impedance signal.

These and other features and functions of the present invention will be more fully understood from the following detailed description, which should be read in light of the accompanying drawings.

DETAILED DESCRIPTION OF THE PREFERRED EMBODIMENTS

Figure 1:
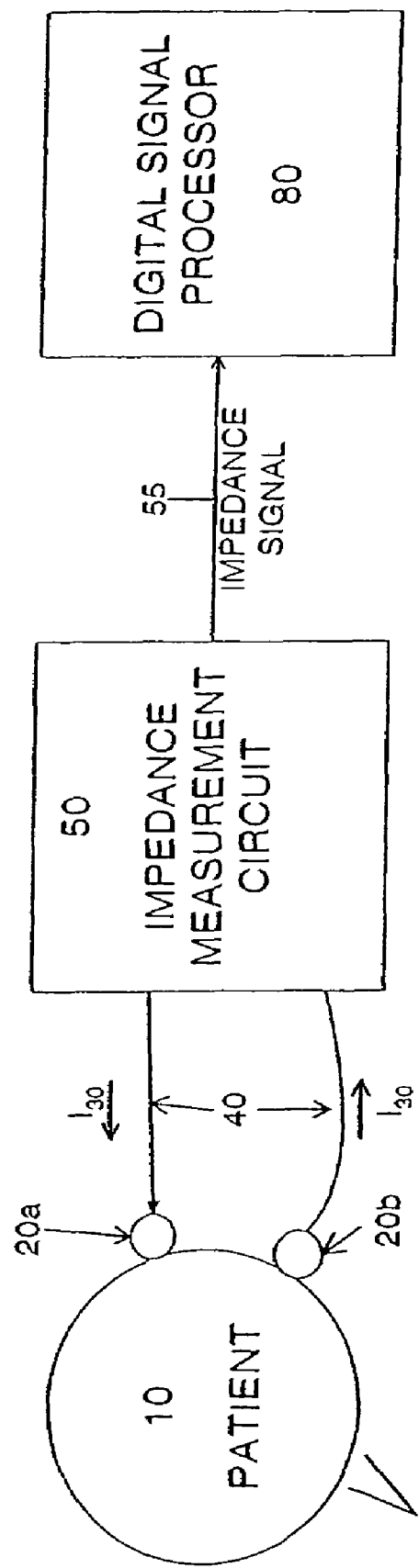
FIG. 1 is a block diagram of the EEG measurement system of the present invention.

Referring to FIG. 1 the EEG measurement system of the present invention is shown attached to a patient 10. Patient 10 is connected through at least two electrodes 20a, 20b to an impedance measurement circuit 50 through lead wires 40. The output 55 of the impedance measurement circuit 50 containing the impedance measurement signal is sent to a digital signal processor 80. The impedance measurement circuit 50 excites the electrodes 20(a), 20(b) by injecting a small current $I_{30}$ into one of the electrodes 20a. The current $I_{30}$ passes through the patient 10 and out the other electrode 20b and back into the impedance measurement circuit 50. This current must be limited to less than 10 microamperes to maintain patient safety. In a preferred embodiment, the signal is approximately 1 nanoampere. At this current level the resulting voltage, according to Ohm's Law, V=IR, is approximately 1 microvolt per kiloohm. The use of this very low excitation current facilitates keeping the resulting voltage very low compared to the biopotential signal being measured. In the case of EEG, such voltages range from hundreds of microvolts down to less than 1 microvolt. In the preferred embodiment, the excitation current is at a frequency just above the EEG band of interest, or 128 Hz.

Figure 2:
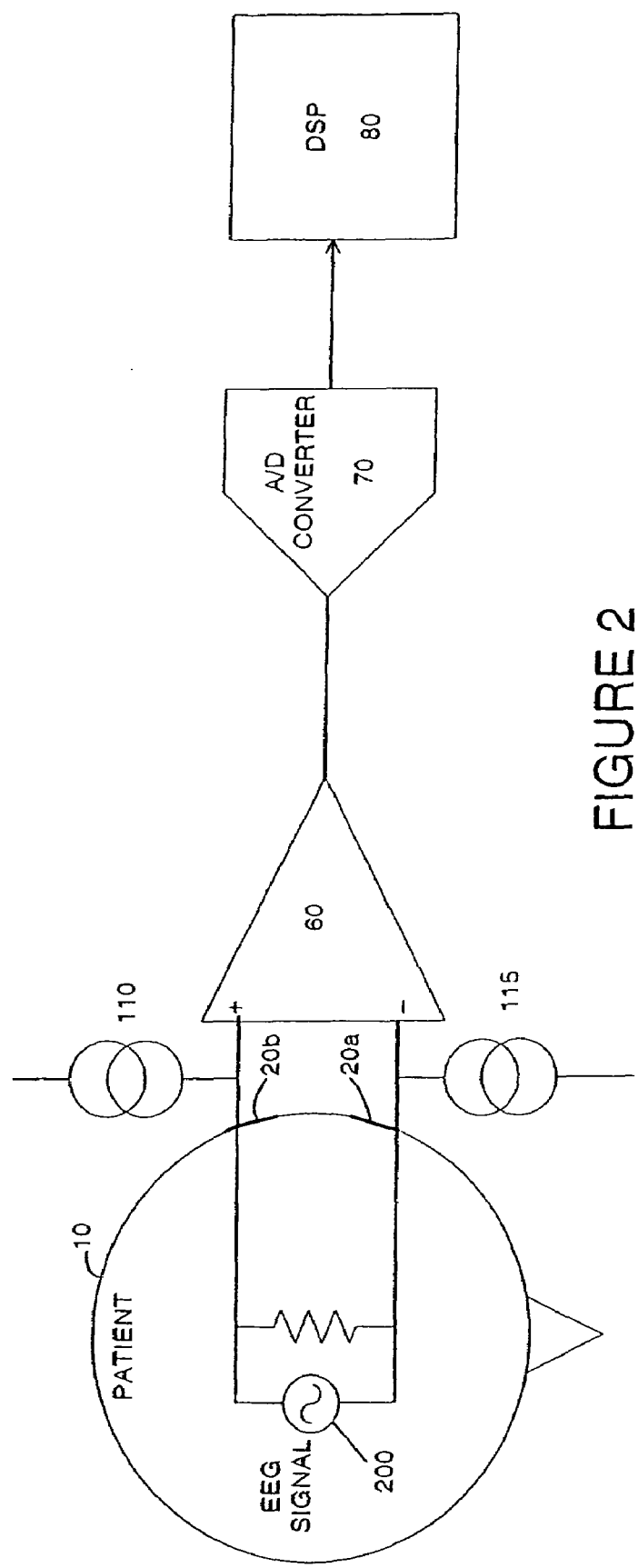
FIG. 2 is a circuit diagram of an electrode impedance measurement circuit used in the EEG measurement system of FIG. 1.

Referring now to FIG. 2, the impedances of the two electrodes 20a, 20b are referred to herein as Zp and Zm. Equal and opposite current sources 110, 115 inject current into the electrode leads 20a, 20b such that the current flows out of the upper current source 110, through the patient 10 and back into the lower current source 115. Instrumentation amplifier 60 has very high input impedance (in a preferred embodiment about 50 megaohms), and so only a negligible current passes through it. The resulting voltage across the inputs of the instrumentation amplifier 60 is equal to the value of the current times the combined impedances Zp, Zm of the two electrodes and the patient 10. This voltage is amplified by the instrumentation amplifier 60 and sent to an analog to digital converter 70. There, the signal is digitized at a sample rate at least exceeding twice the frequency of the excitation current. In a preferred embodiment, the analog to digital converter 70 runs at much higher sampling rate, requiring the use of an over-sampled analog to digital converter. The resulting digitized signal is forwarded to the digital signal processor 80 for computation. In a preferred embodiment, the computation consists of a Fourier transform as described below.

Figure 3:
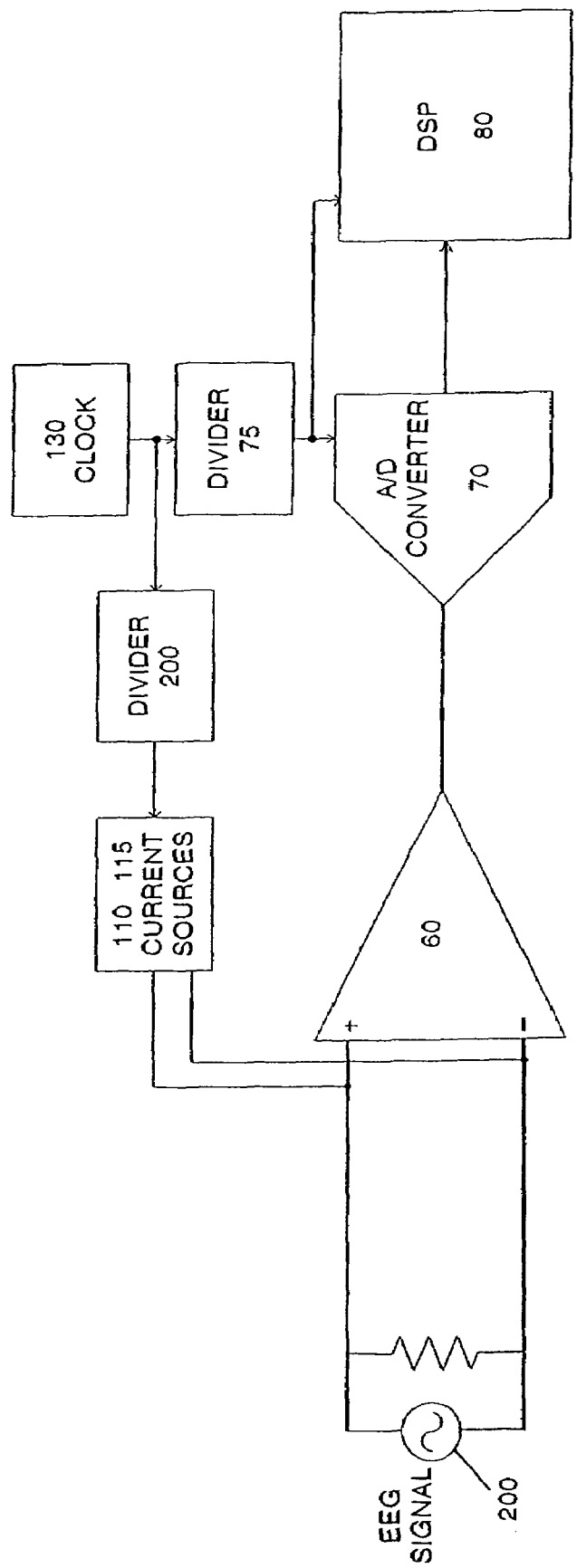
FIG. 3 is a circuit diagram of a clock circuit used in the EEG measurement system of FIG. 1.

FIG. 3 illustrates the synchronization of the frequency of the excitation current sources 110, 115 with the analog to digital converter's 70 sample rate and the digital signal processor's 80 main clock 130.

The frequency of clock 130 is reduced by divider 200, which outputs a pulse train to current sources 110, 115, which generate a current at a frequency that is exactly the clock rate divided by $2^{14}$ or one part in 16,384 of the clock 130. In a preferred embodiment, the clock rate is 2.097152 megahertz, resulting in a signal current that is 128 Hz. The frequency of clock 130 is also reduced by divider 75, which outputs a pulse train to the analog to digital converter 70, which digitizes the impedance measurement signal obtained from the instrumentation amplifier 50. In a preferred embodiment, the digitization occurs at 16,384 times a second, or at a rate of $1/2^7$ or $128^{th}$ of the clock rate. The analog to digital converter 70, therefore, is outputting a digitized version of the impedance test signals at a 16,384 sample per second rate to the digital signal processor 80. The divider 75 also outputs a pulse train to the digital signal processor 80 in the preferred embodiment at 16,384 Hz, again, $128^{th}$ of the clock signal fundamental frequency of 2.097152 megahertz. This enables the digital signal processor 80 to operate at a rate that is an even divisor of the system clock 130, and is exactly synchronous with the frequency of excitation of the current into the electrodes 20a, 20b. The advantage of this technique is that the resulting processed signal is made to be exactly synchronous to the processor clock 130, which enables the processor 80 to execute a form of synchronous detection. The benefits of this approach are that the detection can be done over a very narrow bandwidth (the width of one bin in the discrete Fourier transform DFT), thus filtering out noise over most frequencies and resulting in a more precise measurement. A further benefit is realized because the impedance test stimulus (the excitation current) and the detection (DFT) are always synchronized; thus, no adjustments are needed to make either circuit match the clock of the other.

Figure 4:
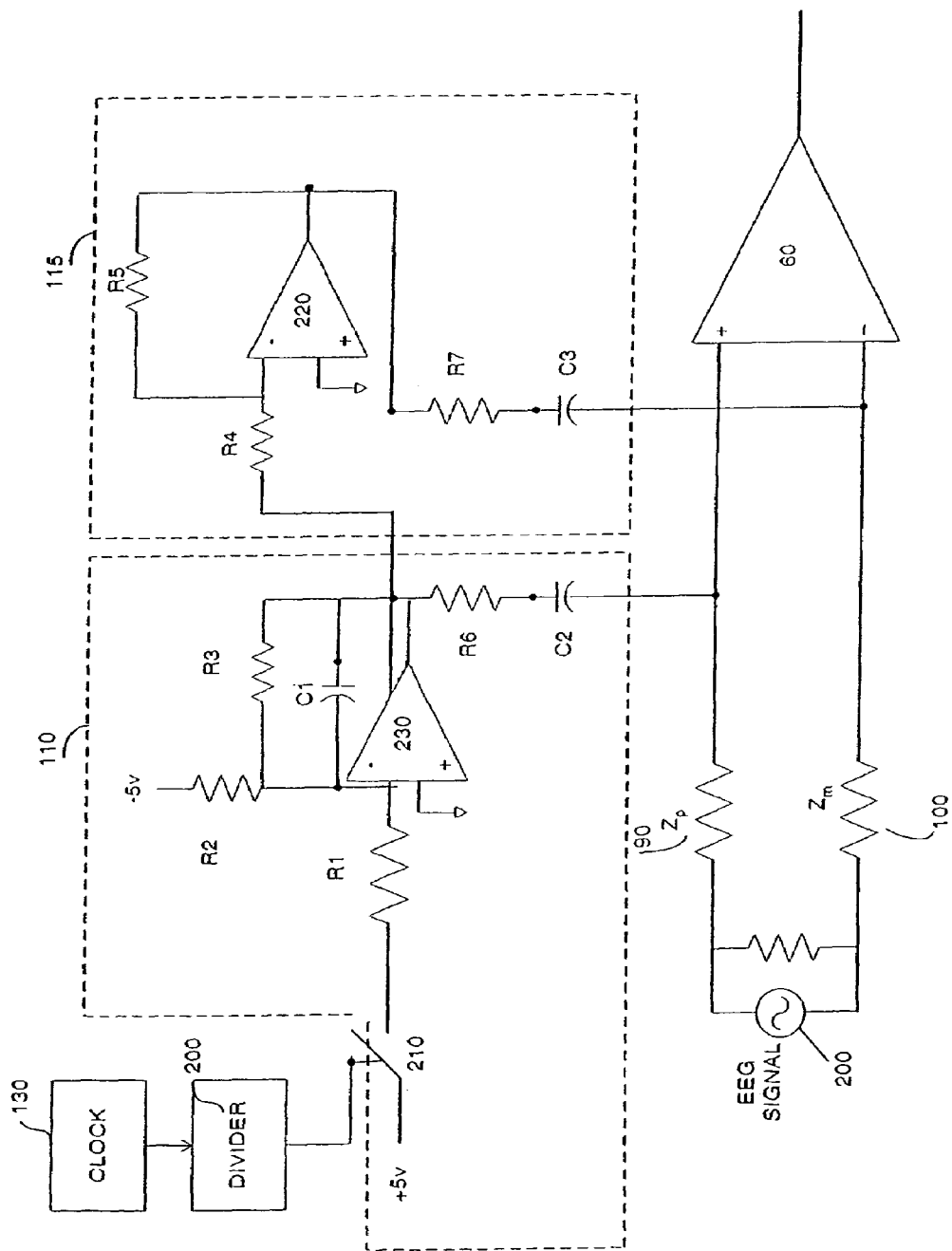
FIG. 4 is a circuit diagram of the impedance test current source circuit used in the clock circuit shown in FIG. 3.

The impedance signal excitation current sources are depicted in FIG. 4. Clock 130 outputs a pulse train with a frequency of 2.0917152 megahertz to divider 200. Divider 200 divides the clock pulse train by $2^{14}$, or 16,384 to provide a 128 Hz clock signal. The digital signal from the divider 200 is output to switch 210, which opens and closes at this 128 Hz rate. This connects and disconnects the +5 volts to resistor R1 at 128 Hz. When the +5 volts is connected by the switch 210 to resistor R1, current flows forward through R1 and into capacitor C1, causing it to build up voltage at the output of operational amplifier 230. When switch 210 opens, the current through resistor R1 and capacitor C1 ceases. The charge on capacitor C1 is now drained through resistor R2 into the −5 volt power supply. The resulting wave shape at the output of operational amplifier 230 is a triangle wave at a repetition rate of 128 Hz. Resistor R3 is needed to maintain the bias for operational amplifier 230. This triangle wave shape is inverted by the operational amplifier circuit comprised of the operational amplifier 220 and resistor network R5 and R4, resulting in a wave shape at the output of operational amplifier 220 that is identical but whose amplitude is opposite in sign to that at the output of operational amplifier 230. The resulting voltages at the outputs of operational amplifiers 230 and 220 are applied to resistors R6 and R7, respectively. These resistors are of a value much greater than the impedances Zp and Zm being measured. In the preferred embodiment they are 4.7 megaohms, much greater than the impedances Zp and Zm, which are typically 0 to 100 kiloohms. The high value resistors R6 and R7 ensure that the excitation current from current source circuits 110, 115 are largely independent of the values of impedances Zp and Zm. The current flowing through resistors R6 and R7 also passes through capacitors C2 and C3. These capacitors serve to block any unwanted direct current and also serve to further increase the apparent output impedance of the current sources. The resulting currents flow through electrodes 20a, 20b, again as depicted in FIG. 2, resulting in a voltage that is proportional to the combined impedance of Zp and Zm, appearing at instrumentation amplifier 60. Thus the voltage at the output of instrumentation amplifier 60 is proportional to the electrode impedances Zp and Zm.

Figure 5A:
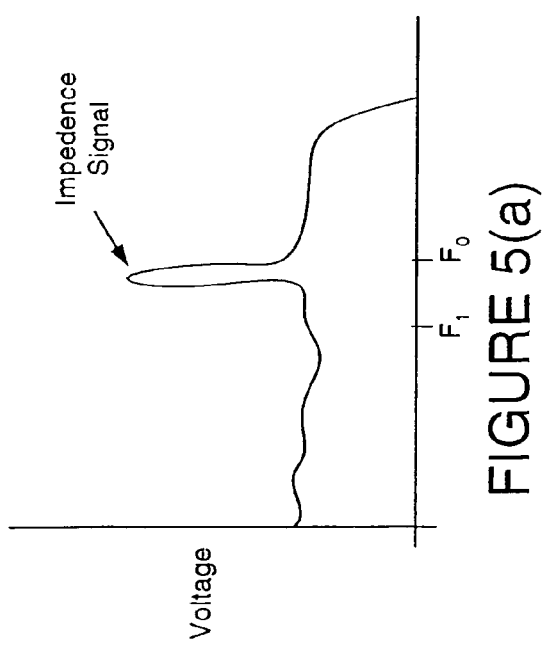
FIGS. 5(a)–5(c) are graphs of the impedance test fast Fourier transforms generated by the EEG measurement system of FIG. 1.
Figure 5B:
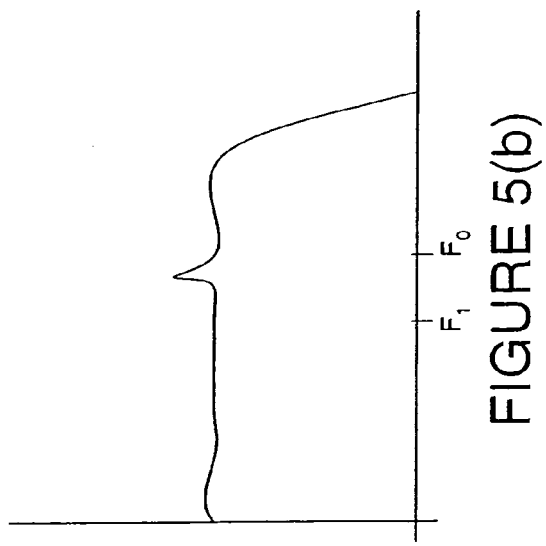
Figure 5C:
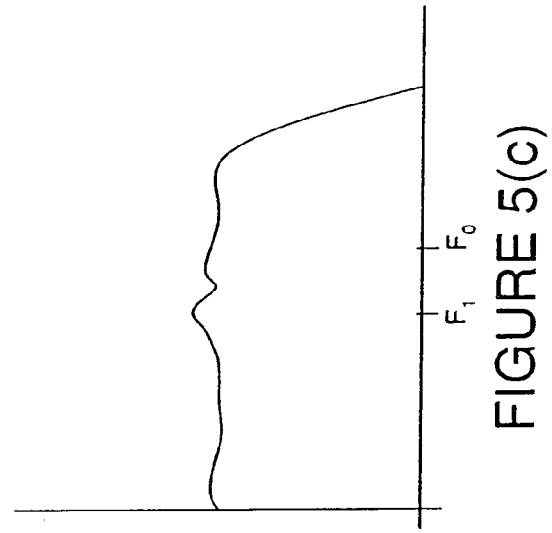

Referring now to FIGS. 5(a)–5(c), a digital signal processing program executed on the digital signal processor 80 executes a fast Fourier transform on the digitized signal. In FIGS. 5(a)–5(c), the Fourier transform is plotted as voltage versus frequency. In FIG. 5(a) the background noise is relatively small, and the impedance signal can be easily seen as a spike arising from the rest of the signal at a frequency $F_0$, which in the preferred embodiment is equal to 128 Hz as described. In this instance its true value is relatively unaffected by the background noise. FIG. 5(b) depicts an instance where the impedance signal is beginning to be obscured by interference and background noise. In terms of the fast Fourier transform of the digitized signal, wide band noise has the effect of raising the voltage across the entire frequency range. This causes the true value to be more effected by the background noise. In FIG. 5(c), the impedance signal is completely obscured by the background noise, causing its true value to be unmeasurable. That is, the Fourier transform value at the excitation frequency is no longer primarily a function of the impedance value, but is more a function of the background noise.

The digital signal processor 80 measures the electrode impedance by measuring the voltage amplitude of the impedance signal and multiplying it by a scale factor to convert the voltage into impedance in Ohms. It can be seen in FIGS. 5(b) and 5(c) that in the presence of noise, this strategy may lead to instances where the derived impedance measurement is not solely a function of the impedance but is more a function of the interference and noise in the rest of the signal. In the present invention, the system discerns this situation by measuring the voltage level at a frequency $F_1$ very close to the impedance frequency $F_0$. The digital signal processor then examines the difference between the voltage at the impedance signal, $F_0$ and the voltage noise signal, $F_1$. If the signal $F_0$ is greater than the signal $F_1$, the impedance measurement is said to have a positive signal to noise ratio. If the signal $F_1$ is greater than the signal $F_0$, the impedance measurement is said to have a negative signal to noise ratio. If the signal to noise ratio is negative, or positive but less than a threshold, the measurement is deemed to be contaminated by interference and background noise.

The digital signal processor 80 may alternatively use other methods to compute the voltage at frequencies $F_0$ and $F_1$. For example, the digital signal processing may execute a discrete Fourier transform (DFT) or use other methods that are known to those skilled in the art. Filters may also be used to measure the amplitude or power of the signal at frequencies $F_0$ and $F_1$. Such filters may be implemented in circuitry or as digital filters in a computer or a dedicated digital signal processing integrated circuit. Further, a wide range of potential signals at frequencies $F_0$ and $F_1$ may be used.

Figure 6:
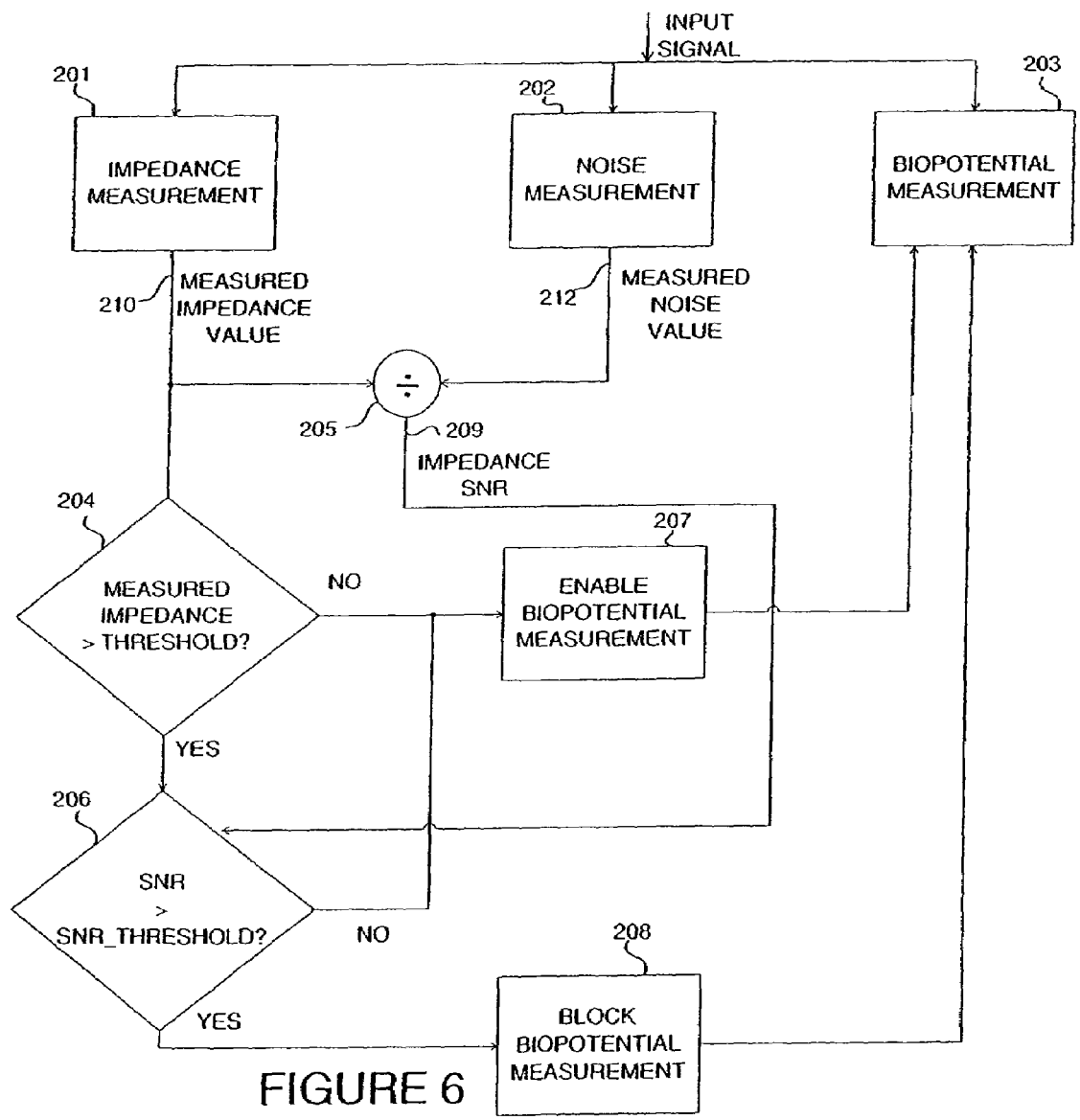
FIG. 6 is a flow chart of the impedance test biopotential measurement process used in the EEG measurement system of FIG. 1.

Referring to FIG. 6, the process implemented by the digital signal processor 80 to measure bioelectric impedance is described. This process may also be executed by any other kind of processor or combination of processors. The digitized signals containing EEG and impedance measurement signals, as well as interference and background noise, are input to the digital signal processor. The impedance measurement is made in step 201, as described earlier, by measuring the voltage at the excitation frequency $F_0$, which is 128 Hz in a preferred embodiment. The impedance measurement is comprised of the actual impedance voltage resulting from the excitation current, plus the contribution from noise. The apparent impedance will be the root of the sum of the squares of the actual impedance plus the noise contribution.

The noise measurement is made in step 202 by measuring the voltage at a frequency $F_1$ or at a set of frequencies very close to the impedance measurement frequency. If a set of frequencies is used, an aggregation function is used to combine the voltages at each of the multiple frequencies. Such aggregation function may be a mean, median, maximum, minimum or other such mathematical function well known in the art. In addition, the voltages at each of the multiple frequencies may be weighted to increase the contribution of certain frequencies over others. In the preferred embodiment, this noise measurement is the root mean square (RMS) of the signal voltage in frequency range from 70 to 110 Hz. This is beneficial since the RMS voltage may be used elsewhere in the EEG system for detecting the presence of electromyogram (EMG) signals, reducing the amount of computation required of the digital signal processor 80. The biopotential measurement 203 in a preferred embodiment is the EEG. In a preferred embodiment, the EEG signal is used to calculate the depth of consciousness of a patient undergoing anesthesia using Bispectral Index monitoring.

The measured impedance value 210 is divided by the measured noise value 212 in step 205 to form the impedance signal to noise ratio (SNR) 209. The ongoing biopotential signal is a contributor to the noise in the impedance measurement process.

The measured impedance value 210 is compared against a threshold limit in step 204. In a preferred embodiment, the threshold limit is 15 K Ohms. If the measured impedance value 210 is less than or equal to the threshold, then it is known that the actual impedance is less than the threshold regardless of the background noise, and the biopotential measurement 203 is enabled in step 207. If the measured impedance value 210 is greater than the threshold limit, as determined in step 204, then the actual impedance may or may not be greater then the threshold. In this case the impedance signal to noise ratio 209 is tested against the SNR threshold in step 206 to determine if background noise has increased the measured impedance to a value greater than that of the actual impedance value. If the impedance SNR is greater than the SNR threshold, the impedance measurement is deemed to be uncontaminated by noise. In this case, the biopotential measurement is blocked in step 208 as it is deemed that the impedance is too high to make an accurate biopotential measurement. In the case where the impedance SNR is less than or equal to the SNR threshold, then the impedance measurement is deemed to be invalid and, and the biopotential measurement continues to be enabled in step 207.

The impedance measurement is most susceptible to contamination by noise when the actual impedance is close to the threshold limit. This is the interval for which the smallest amount of noise may cause an acceptable impedance to appear to be unacceptably high. In the preferred embodiment, the value of the SNR threshold is adjusted so that an actual impedance that is approximately 15% below the impedance threshold would not be subject to contamination by noise that results in the blocking of the biopotential measurement. For example, in the preferred embodiment the SNR threshold is set so an actual impedance of 13 kiloohm will not appear to be greater than the impedance limit of 15 kiloohm in the presence of noise. Thus the noise voltage limit is set by the following equation:

$$\text{max noise voltage} = \text{sqrt}((15 \text{ kiloohm} * 1 \text{ nanoampere})^2 - (13 \text{ kiloohm} * 1 \text{ nanoampere})^2) = 7.5 \text{ microvolt}$$

The SNR threshold is then:

$$SNR = 20 * \log((13 \text{ kiloohm} * 1 \text{ nanoampere})/7.5 \text{ microvolt}) = 4.8 \text{ decibels.}$$

While the foregoing invention has been described with reference to its preferred embodiments, various alterations and modifications will occur to those skilled in the art. All such alterations and modifications are intended to fall within the scope of the appended claims.

What is claimed is:

1. A system for measuring bioelectric impedance in a biopotential measurement system and determining the validity of said impedance measurement including at least two electrodes, said system comprising:

a first current source for injecting a first current into one of the at least two electrodes;

a second current source for injecting a second current into a second of the at least two electrodes, said second current being equal to said first current and having a polarity opposite said first current;

an instrumentation amplifier having a high input impedance, said amplifier amplifying an impedance signal resulting from said first and second currents; and a processor for computing an impedance signal to noise ratio and determining the validity of the bioelectric impedance measurement by comparing said impedance signal to noise ratio against an impedance signal to noise ratio threshold value.

2. The system for measuring bioelectric impedance and determining the validity of said impedance measurement of claim 1 further comprising:

an analog to digital converter connected to said instrumentation amplifier for converting said impedance signal from said instrumentation amplifier into a digital impedance signal; and a clock connected to said first and second current sources and to said analog to digital converter to synchronize the frequency of injection of said first and second currents with a sample rate of said analog to digital converter.

3. A system for measuring bioelectric impedance in a biopotential measurement system and determining the validity of said impedance measurement including at least two electrodes, said system comprising:

a first current source for injecting a first current into one of the at least two electrodes;

a second current source for injecting a second current into a second of the at least two electrodes, said second current being equal to said first current and having a polarity opposite said first current;

an instrumentation amplifier having a high input impedance, said amplifier amplifying an impedance signal resulting from said first and second currents;

a processor for determining if said impedance signal is contaminated by noise;

an analog to digital converter connected to said instrumentation amplifier for converting said impedance signal from said instrumentation amplifier into a digital impedance signal;

a clock connected to said first and second current sources and to said analog to digital converter to synchronize the frequency of injection of said first and second currents with a sample rate of said analog to digital converter;

a first divider for outputting a first pulse train to said first current source and said second current source to cause said first current source and said second current source to generate a current at a selected frequency; and a second divider for outputting a second pulse train to said analog to digital converter and said processor to cause said processor to operate synchronously with said first current source and said second current source.

4. A system for measuring bioelectric impedance in a biopotential measurement system and determining the validity of said impedance measurement including at least two electrodes, said system comprising:

a first current source for injecting a first current into one of the at least two electrodes;

a second current source for injecting a second current into a second of the at least two electrodes, said second current being equal to said first current and having a polarity opposite said first current;

an instrumentation amplifier having a high input impedance, said amplifier amplifying an impedance signal resulting from said first and second currents; and a processor for determining if said impedance signal is contaminated by noise, wherein said processor computes an impedance signal to noise ratio, compares said impedance signal to a threshold impedance limit and, if said impedance signal is greater than said threshold impedance limit, compares said impedance signal to noise ratio to a threshold signal to noise ratio to determine if background noise has increased said impedance signal.

* * * * *